United States Patent [19]
Yankielun et al.

[11] Patent Number: 5,841,289
[45] Date of Patent: Nov. 24, 1998

[54] SYSTEM AND METHOD FOR DETECTING ACCRETION OF FRAZIL ICE ON UNDERWATER GRATINGS

[75] Inventors: Norbert E. Yankielun, Lebanon; John J. Gagnon, Enfield, both of N.H.

[73] Assignee: The United States of America as represented by the Secretary of the Army, Washington, D.C.

[21] Appl. No.: 789,889

[22] Filed: Jan. 28, 1997

[51] Int. Cl.⁶ .................................................. G01R 27/04
[52] U.S. Cl. ........................ 324/639; 324/643; 340/580
[58] Field of Search ............................ 266/44; 324/534, 324/674, 643, 642, 639; 340/580; 333/253

[56] References Cited

U.S. PATENT DOCUMENTS

| | | | |
|---|---|---|---|
| 3,789,296 | 1/1974 | Caruso | 324/643 |
| 3,873,927 | 3/1975 | Overall | 328/8 |
| 4,054,255 | 10/1977 | Magenheim | 244/134 |
| 4,296,397 | 10/1981 | Strimple | 266/44 |
| 4,819,480 | 4/1989 | Sabin | 73/170 R |
| 4,914,394 | 4/1990 | Meyer | 324/534 |
| 5,062,120 | 10/1991 | Daly et al. | 374/143 |
| 5,134,380 | 7/1992 | Jonas | 324/674 |
| 5,381,694 | 1/1995 | Glynn et al. | 73/627 |
| 5,467,944 | 11/1995 | Luukkala | 244/134 F |
| 5,521,584 | 5/1996 | Ortolano et al. | 340/581 |
| 5,554,936 | 9/1996 | Mohr | 324/642 |

Primary Examiner—Ernest F. Karlsen
Assistant Examiner—Thomas Valone
Attorney, Agent, or Firm—Luther A. Marsh

[57] ABSTRACT

A system for detecting accretion of frazil ice on underwater gratings comprises a pair of parallel electrically conductive bars mounted side-by-side, for disposition beneath a water surface and spaced from but proximate an underwater intake grating. The system further includes a coaxial transmission line connected at a first end to the pair of bars for extension from the bars upwardly above the water surface, and a time domain reflectometer disposed above the water surface for generating electromagnetic pulses and having a second end of the transmission line fixed thereto. The transmission line facilitates propagation of the pulses to the bars for further travel to distal ends of the bars, and back to the reflectometer. The reflectometer is adapted to compute pulse round trip travel time in the bars and to compute changes in the round trip travel time, from which can be determined absence, presence, and build-up of frazil ice on the bars, providing an indication of same on the grating.

The invention further contemplates a method for detecting accretion of frazil ice on underwater gratings, utilizing the above-described system.

5 Claims, 1 Drawing Sheet

SYSTEM AND METHOD FOR DETECTING ACCRETION OF FRAZIL ICE ON UNDERWATER GRATINGS

BACKGROUND OF THE INVENTION

1. Field of the Invention

This invention relates to the icing up of underwater intake gratings in cold water, and is directed more particularly to a reliable and economical system and method for monitoring ice build-up from a remote convenient location.

2. Description of the Prior Art

Industrial, commercial and municipal facilities located in regions subject to seasonal freezing, and which are required to draw quantities of water from rivers during the freezing seasons, are subject to the deleterious effects of buildup of frazil ice on gratings protecting water intakes from ingestion of foreign objects and aquatic life. The effects can include, depending on the nature of the facility in question, lower operating efficiencies, loss of cooling water, damage to pumps and other components, and loss of revenues because of down time.

"Frazil ice" is formed when turbulent water is cooled. Once the water is supercooled a few hundredths of a degree, minute ice crystals form in the water and conglomerate, resulting in flocks of frazil ice. Frazil ice forms mainly in rivers, but has been experienced in lakes, cooling ponds, and even in the ocean. Many water intakes for power generation plants and other industrial and commercial processing plants have waterway approaches that are subject to turbulent flow, a prime condition for the formation of frazil ice. As long as the water temperature is at, or below, freezing, it is possible for frazil ice to form. Once formed, frazil ice adheres to, and continues to accrete on, virtually any natural or man-made object in the water, including rocks, wood, and metal structures, and including protective gratings over water intakes. Water intakes have been known to completely occlude in a matter of a few hours.

Currently, the only detection and alarm systems in implementation consist of complex, mechanical systems with moving components, having low reliability and requiring significant maintenance. There is thus a need for a simple, economical, reliable, and low maintenance system for detection and monitoring of growth of frazil ice on water intake gratings.

SUMMARY OF THE INVENTION

Accordingly, an object of the invention is to provide a system for detecting and monitoring accretion of frazil ice on underwater gratings, which system is devoid of moving mechanical parts, is reliable, economical, and requires little maintenance.

A further object of the invention is to provide a method for detecting and monitoring accretion of frazil ice on underwater gratings, which method is simple and reliable in operation.

With the above and other objects in view, as will hereinafter appear, a feature of the present invention is the provision of a system for detecting accretion of frazil ice on underwater gratings, the system comprising a pair of parallel electrical conductive bars mounted side-by-side, for disposition beneath a water surface and spaced from but proximate an underwater intake grating. The system further comprises a coaxial transmission line connected at a first end thereof to the pair of bars for extension from the bars upwardly above the water surface, and a time domain reflectometer for disposal above the water surface and for generating electromagnetic pulses, the reflectometer having a second end of the transmission line fixed thereto. The transmission line facilitates propagation of the pulses to the bars for further travel to distal ends of the bars and back to the reflectometer. The reflectometer is adapted to compute round trip travel time of the pulses in the bars and to compute changes in the round trip travel time, from which can be determined absence, presence, and build-up of frazil ice on the bars, which is substantially equal to the same on the grating.

In accordance with a further feature of the invention, there is provided a method for detecting accretion of frazil ice on an underwater grating, the method comprising the steps of providing a pair of parallel electrically conductive bars mounted side-by-side and substantially co-extensive, providing a time domain reflectometer, connecting a first end of a coaxial transmission line to the bars and a second end of the coaxial transmission line to the reflectometer, positioning the bars beneath the surface of the water, proximate and spaced from the grating, and positioning the reflectometer above the surface of the water and remote from the bars. The method further comprises the steps of actuating the reflectometer to send electromagnetic pulses through the transmission line and through the bars to distal ends of the bars, the bars and the transmission line facilitating return of the pulses to the reflectometer, and, using the reflectometer, computing time of round trip travel of the pulses in the bars, determining changes in pulse round trip times, and therefrom determining absence, presence and build-up of frazil ice on the bars to thereby provide an indication of the same on the grating.

The above and other features of the invention, including various novel details of construction and combinations of parts, will now be more particularly described with reference to the accompanying drawings and pointed out in the claims. It will be understood that the particular devices and methods embodying the invention are shown by way of illustration only and not as limitations of the invention. The principles and features of this invention may be employed in various and numerous embodiments without departing from the scope of the invention.

BRIEF DESCRIPTION OF THE DRAWINGS

Reference is made to the accompanying drawings in which are shown illustrative embodiments of the invention, from which its novel features and advantages will be apparent.

In the drawings.

DESCRIPTION OF THE PREFERRED EMBODIMENTS

Figure 1:
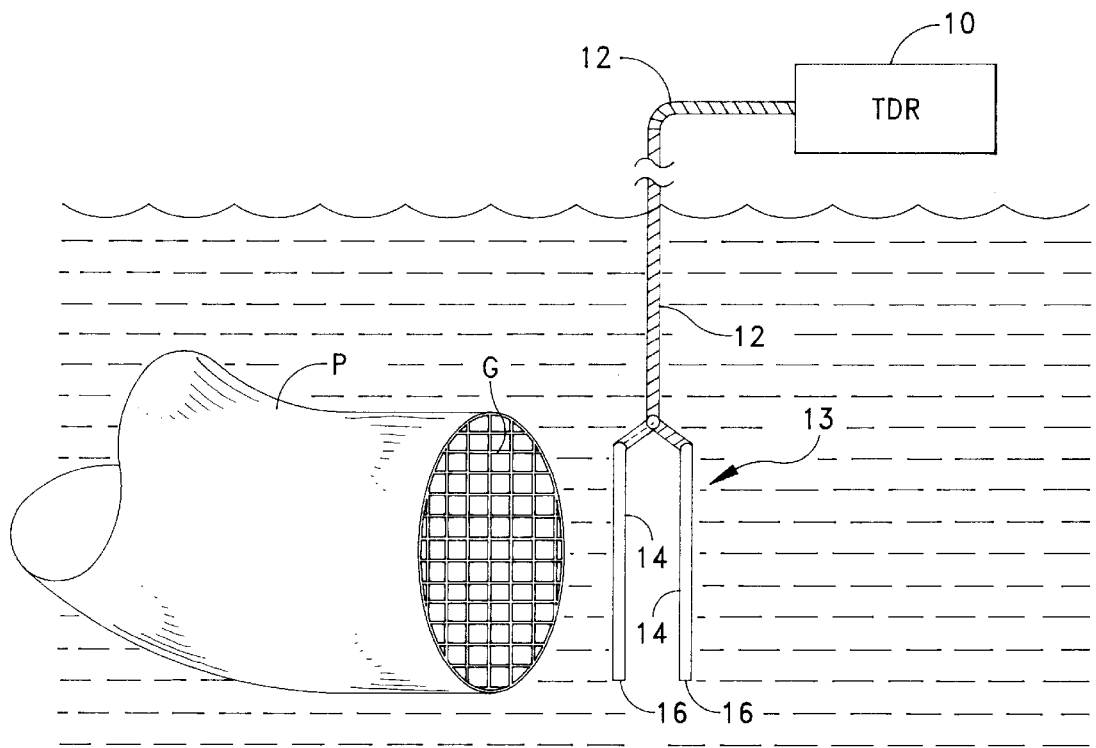
FIG. 1 is a diagrammatic view of one form of system illustrative of an embodiment of the invention.

In this invention a known instrument commonly referred to as "Time Domain Reflectometer" (TDR) 10, is connected by means of a coaxial transmission line 12 to a parallel metal rod sensor 13, consisting of two, parallel metal rods 14 (FIG. 1). The operative principle of the TDR is known, is described in the technical literature, and is applied to numerous measurement and testing applications. The TDR 10 operates by generating an electromagnetic pulse and coupling it to the transmission line 12. The pulse propagates down the transmission line 12 at a fixed and calculable velocity, a function of the speed of light, and the electrical and physical characteristics of the transmission line 12. The pulse travels down the transmission line 12 and the rods 14 until the ends 16 of the rods 14 are reached, and then is reflected back to the TDR 10.

The time t, in seconds, that it takes for the pulse to propagate down and back the length of the parallel metal rod sensor 13 (travel time in the transmission line 12 is discounted) is called the "round trip travel time" and is calculated as:

$$t = 2L/v$$

wherein:
L=length of the parallel metal rod sensor (m); and
V=velocity of propagation (m/s)
The propagation velocity can be given as:

$$v = c/\sqrt{\epsilon} = c/n$$

wherein:
c=velocity of light in free space ($3 \times 10^8$ m/s);
$\epsilon$=the relative dielectric constant of the media surrounding the transmission line; and
n=index of refraction of the media surrounding the transmission line.

In freshwater $\epsilon=80$ and n=9; in solid freshwater ice $\epsilon=3.12$ and n=1.78. Frazil ice immersed in liquid water has a dielectric constant which is a mixture of those of water and ice. This mixture may not always have a constant value in all formation and accretion situations, but in all cases the bulk dielectric (bulk index of refraction) of the mixture is less than that of liquid water alone. Therefore, as frazil ice accretes on the metal rod sensor 13, the bulk dielectric constant of the water/ice in immediate proximity to the sensor 13 decreases and the propagation velocity of the sensor 13 increases, proportionally decreasing the sensor round trip travel time. It is the decrease in round trip travel time that is measurable by the TDR, and is used to indicate the absence, presence or buildup of frazil ice volume on the bars, which is substantially equal to the same conditions on the nearby gratings, or other submerged structures of interest.

In operation, the parallel metal rod sensor 13 is immersed in water in close proximity, but not in electrical contact, with a grating G protecting a water input pipe P (FIG. 1) An initial reference reading is made of the round trip travel time for a pulse propagating along the metal rod sensor 13 when the sensor is in an ice free state. This data is stored in TDR computer memory. Thereafter, pulses are generated serially and subsequent pulse propagation times are frequently and automatically compared with the original reference value. As frazil ice attaches to and builds up on and around the parallel metal rod sensor 13, the round-trip travel time for the pulse becomes shorter. A real-time computer algorithm is used to compare the reference round trip travel time with subsequent values, trigger an alarm when a threshold difference in round trip travel times is reached, and signal that maintenance action should be taken to free the intake gratings of frazil ice. In view of the proximity of the sensor 13 to the grating G, any detected accretion of ice on and around the bars 14 is indicative of similar accretion on the grating G.

Figure 2:
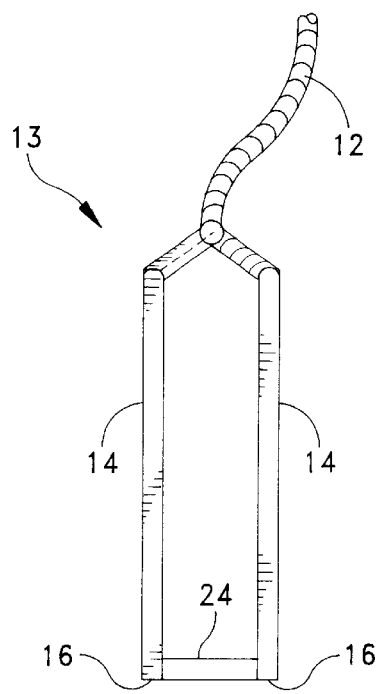
FIG. 2 is a front elevational view of an alternative embodiment of a portion of the system of FIG. 1.
Figure 3:
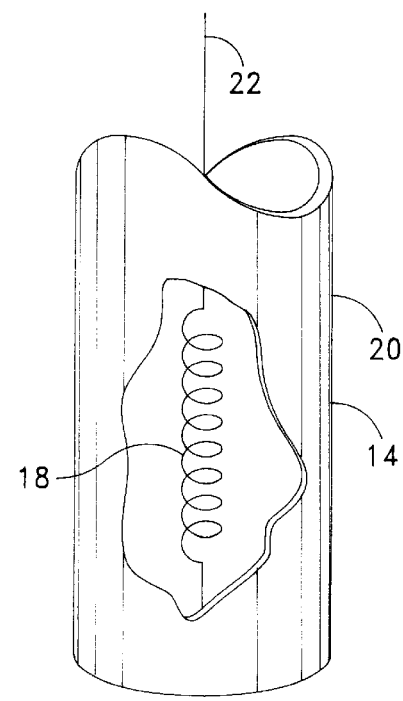
FIG. 3 is an elevational, broken away, view of an alternative embodiment of a portion of the system of FIG. 1

The sensor 13 can be cleared of frazil ice buildup in several ways. The sensor can be mechanically cleared by maintenance personnel while clearing the intake gratings. There are also at least two methods by which the sensor can be electrically cleared. If the sensor is fabricated using two parallel metallic tubes 20 (one shown in FIG. 3), instead of solid rods, electrical heating elements 18 can be placed internally of the rods 14 and activated through a power line 22 as appropriate. Additionally, based on transmission line theory, the distal ends 16 of the sensor rods 14 may be open circuited (FIG. 1) or permanently shorted together by a third rod 24 (FIG. 2), without affecting pulse propagation. By choosing a distally shorted transmission line for the sensor (FIG. 2), a high current may be applied to the transmission line to impart heat thereto and clear any frazil ice buildup.

There may be circumstances in which foreign objects (e.g., rag, plastic bag, log, etc.) come into contact with the frazil sensor and produce a false indication of ice accretion. To decrease the probability of a false indication, a temperature sensor (not shown) may be co-located with the fazil ice sensor. The output of the temperature sensor can be used in conjunction with the TDR data to verify the presence of frazil ice. That is, if the temperature sensor detects ambient water temperature at the submerged frazil probe inconsistent with supercooled water, then it can be surmised that frazil ice has not formed.

As a further confirmation of the presence of frazil ice growth vs. false reading from some foreign material impinged against the frazil ice sensor, the sensor can be briefly heated in an attempt to melt any frazil accretion. If a change in TDR signature, before and after heating, is noticed, then it can be concluded that the sensor was accreted with frazil. If the signature remains the same prior to, and after, heating, then there is a high probability that the sensor is fouled by a foreign object and requires maintenance.

There is thus provided a system providing remote and continuous monitoring, no moving mechanical parts, low maintenance, and simple installation and operation. Further, in due course, only the sensor 13 of the system will require periodic replacement and the sensor is a low-cost item.

It is to be understood that the present invention is by no means limited to the particular construction herein disclosed and/or shown in the drawings, but also comprises any modifications or equivalents within the scope of the claims.

Having thus described our invention, what we claim as new and desire to secure by Letters Patent of the United States:

1. A method for detecting accretion of frazil ice on an underwater grating, said method comprising the steps of:
providing a pair of parallel electrically conductive bars mounted side-by-side and substantially co-extensive;
providing a time domain reflectometer;
connecting a first end of a coaxial transmission line to said bars and a second end of said coaxial transmission line to said reflectometer;
positioning said bars and said transmission line first end beneath the surface of the water, proximate and spaced from the grating, with said bars depending from said transmission line and having free distal ends extending downwardly and free floating;
positioning said reflectometer above the surface of the water and remote from said bars;
actuating said reflectometer to send electromagnetic pulses through said transmission line and through said bars to said distal ends of said bars, said bars and said transmission line facilitating return of the pulses to said reflectometer;

computing round trip time of travel of said pulses in said bars, and determining changes in pulse round trip times, and therefrom determining absence, presence and build-up of frazil ice volume on and around said bars;

thereby to obtain an indication of same on said grating.

2. The method in accordance with claim 1 wherein said bars are interconnected at distal ends thereof by a third bar.

3. The method in accordance with claim 1 wherein a heating coil is disposed in each of said bars.

4. The method in accordance with claim 3 including the further step of providing electrical current to each of said heating coils to heat said bars to remove ice therefrom.

5. The method in accordance with claim 1 wherein said pulses are sent from said reflectometer serially.

* * * * *